(12) United States Patent
Busch (10) Patent No.: US 7,131,333 B2
(45) Date of Patent: Nov. 7, 2006

(54) PULSE ECHO ULTRASONIC TEST CHAMBER FOR TRAY PRODUCTION SYSTEM

(75) Inventor: Ralph E. Busch, Olney, MD (US)

(73) Assignee: Sonix, Inc., Springfield, VA (US)

( * ) Notice: Subject to any disclaimer, the term of this patent is extended or adjusted under 35 U.S.C. 154(b) by 0 days.

(21) Appl. No.: 10/842,087

(22) Filed: May 10, 2004

(65) Prior Publication Data

US 2004/0206180 A1    Oct. 21, 2004

Related U.S. Application Data (63) Continuation-in-part of application No. 10/387,881, filed on Mar. 13, 2003.

(60) Provisional application No. 60/396,347, filed on Jul. 16, 2002.

(51) Int. Cl.
*G01N 29/00* (2006.01)

(52) U.S. Cl. .......................... 73/620; 73/644

(58) Field of Classification Search .................. 73/606, 73/618, 620, 608, 642, 644, 600, 629, 627, 73/633, 622, 628; 34/60

See application file for complete search history.

(56) References Cited

U.S. PATENT DOCUMENTS

| | | | |
|---|---|---|---|
| 3,063,290 A | 11/1962 | Kaserman et al. | |
| 3,489,608 A | 1/1970 | Jacobs et al. | |
| 3,558,093 A | 1/1971 | Bok | |
| 3,617,045 A | 11/1971 | DaCosta et al. | |
| 3,678,735 A | 7/1972 | Boulanger et al. | |
| 3,737,573 A | 6/1973 | Kessler | |
| 3,760,822 A | 9/1973 | Evans | |
| 3,765,431 A | 10/1973 | Jannett et al. | |
| 3,790,281 A | 2/1974 | Kessler et al. | |
| 3,850,027 A | 11/1974 | Nakanishi et al. | |
| 3,886,793 A | 6/1975 | Cramer et al. | |
| 3,898,839 A | 8/1975 | White | |
| 3,988,196 A | 10/1976 | Wanesky | |
| 4,008,602 A | 2/1977 | Love | |
| 4,012,951 A | 3/1977 | Kessler | |
| 4,058,000 A | 11/1977 | Ries et al. | |
| 4,164,150 A | 8/1979 | Ries et al. | |
| 4,208,915 A | 6/1980 | Edwards | |
| 4,238,962 A | 12/1980 | Taenzer | |
| 4,252,125 A | 2/1981 | Iinuma | |
| 4,316,271 A | 2/1982 | Evert | |
| 4,332,016 A | 5/1982 | Berntsen | |
| 4,344,448 A | 8/1982 | Potts | |
| 4,472,975 A | 9/1984 | Beck et al. | |
| 4,517,985 A | 5/1985 | Teslawski et al. | |
| 4,518,992 A * | 5/1985 | Kessler et al. | ............. 348/163 |
| 4,526,038 A | 7/1985 | Box et al. | |
| 4,543,130 A | 9/1985 | Schwartzman | |
| 4,662,215 A | 5/1987 | Eckert | |
| 4,781,067 A | 11/1988 | Cichanski | |
| 4,807,634 A | 2/1989 | Enjoji et al. | |
| 4,854,337 A | 8/1989 | Bunkenburg et al. | |
| 4,866,986 A | 9/1989 | Cichanski | |

(Continued)

*Primary Examiner*—Hezron Williams
*Assistant Examiner*—Jacques Saint-Surin (57) ABSTRACT

A method and apparatus for retaining a part in a carrier during an ultrasonic scan. The part is positioned above a first opening in a lower chamber while air is drawn out of a second opening in the lower chamber to apply suction to the lower surface of the part. An ultrasonic transducer is housed in an upper chamber that dispenses coupling fluid to the top surface of the object.

21 Claims, 6 Drawing Sheets

U.S. PATENT DOCUMENTS

| | | | |
|---|---|---|---|
| 4,920,803 A * | 5/1990 | Karaki et al. | 73/606 |
| 4,924,707 A | 5/1990 | Kliesch | |
| 4,977,779 A * | 12/1990 | Karaki et al. | 73/606 |
| 5,014,711 A | 5/1991 | Nagasaki | |
| 5,060,517 A | 10/1991 | Fushimi et al. | |
| 5,077,695 A | 12/1991 | Khuri-yakub et al. | |
| 5,117,697 A | 6/1992 | Takishita et al. | |
| 5,195,729 A | 3/1993 | Thomas et al. | |
| 5,212,987 A * | 5/1993 | Dransfeld et al. | 73/579 |
| 5,240,522 A | 8/1993 | Tanaka et al. | |
| 5,301,552 A | 4/1994 | Nagura et al. | |
| 5,320,225 A | 6/1994 | Kirkpatrick | |
| 5,359,895 A | 11/1994 | Isenberg et al. | |
| 5,374,021 A | 12/1994 | Kleinman | |
| 5,374,829 A | 12/1994 | Sakamoto et al. | |
| 5,431,054 A | 7/1995 | Reeves et al. | |
| 5,469,742 A | 11/1995 | Lee et al. | |
| 5,531,119 A | 7/1996 | Meyers | |
| 5,585,564 A | 12/1996 | Brunty et al. | |
| 5,600,068 A | 2/1997 | Kessler et al. | |
| 5,629,865 A | 5/1997 | Roth | |
| 5,646,351 A | 7/1997 | Good et al. | |
| 5,668,452 A | 9/1997 | Villarreal et al. | |
| 5,684,252 A | 11/1997 | Kessler et al. | |
| 5,874,319 A | 2/1999 | Dunaway et al. | |
| 5,922,961 A * | 7/1999 | Hsu et al. | 73/606 |
| 5,948,985 A | 9/1999 | Brautigan et al. | |
| 5,996,415 A | 12/1999 | Stanke et al. | |
| 6,027,605 A | 2/2000 | Lehmann et al. | |
| 6,062,084 A | 5/2000 | Chang et al. | |
| 6,085,591 A | 7/2000 | Mallard | |
| 6,089,095 A | 7/2000 | Yang et al. | |
| 6,227,946 B1 | 5/2001 | Gonzales-Martin et al. | |
| 6,230,896 B1 | 5/2001 | Lambert | |
| 6,261,370 B1 | 7/2001 | Otsuki et al. | |
| 6,357,136 B1 * | 3/2002 | Erickson et al. | 34/60 |
| 6,460,414 B1 * | 10/2002 | Erickson et al. | 73/603 |
| 6,513,796 B1 | 2/2003 | Leidy et al. | |
| 6,524,351 B1 | 2/2003 | Ohta | |
| 6,540,014 B1 | 4/2003 | Getchel et al. | |
| 6,603,103 B1 | 8/2003 | Ulrich et al. | |
| 6,709,877 B1 | 3/2004 | Tsui et al. | |
| 6,712,765 B1 | 3/2004 | Glenn | |
| 6,743,296 B1 | 6/2004 | Kao | |
| 6,880,387 B1 | 4/2005 | Kessler et al. | |
| 6,890,302 B1 | 5/2005 | Oravez et al. | |
| 6,895,820 B1 | 5/2005 | Oravez et al. | |
| 6,912,908 B1 | 7/2005 | Kessler et al. | |
| 6,921,672 B1 | 7/2005 | Satya et al. | |

* cited by examiner

PULSE ECHO ULTRASONIC TEST CHAMBER FOR TRAY PRODUCTION SYSTEM

PRIORITY CLAIM

The application is a continuation-in-part of application Ser. No. 10/387,881 titled "Ultrasonic Test Chamber For Tray Production System and the Like" filed Mar. 13, 2003, which in turn clams priority to provisional application No. 60/396,347 titled "Ultrasonic Test Chamber for Tray Production System" filed Jul. 16, 2002.

FIELD OF THE INVENTION

This invention relates generally to the field of ultrasonic testing. More particularly, this invention relates to a system and method for ultrasonic inspection of parts in tray production system.

BACKGROUND

Non-destructive inspection of parts has been used for many years. More recently, ultrasonic inspection has been extended to small parts such as integrated circuits or other electronic components. During the manufacture of Integrated Circuits, the parts are often loosely arranged in trays or carriers to facilitate transfer of the parts through the production process. In order to prevent delays in the production process, an ultrasonic tester that can accommodate trays of parts is required.

An ultrasonic tester may include three sections. The first section is a de-bubbling area where the parts in the carriers are wetted and air bubbles are removed. The normal convention is to submerge the parts and 'wiggle' them to remove the air bubbles. The second section is a scanning station where wetted and bubble free parts are ultrasonically scanned. In order to complete the scan in a short time, the ultrasonic transducer must be moved across the parts at high speed in close proximity to the parts. The result is a motion in the fluid that tends to move the parts in the carriers or dislodge them from the carrier. The third section is a drying area, where a gas stream is used to dry any residual coupling fluid from the parts. Typically compressed and/or heated air is directed across the parts. Each of these processes tends to dislodge the parts when they are loosely arranged in a tray or carrier.

BRIEF DESCRIPTION OF THE DRAWINGS

The novel features believed characteristic of the invention are set forth in the appended claims. The invention itself, however, as well as the preferred mode of use, and further objects and advantages thereof, will best be understood by reference to the following detailed description of an illustrative embodiment when read in conjunction with the accompanying drawing(s), wherein:

DETAILED DESCRIPTION

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the description below, like reference numerals are used to describe the same, similar or corresponding parts in the several Views of the drawings.

Figure 1:
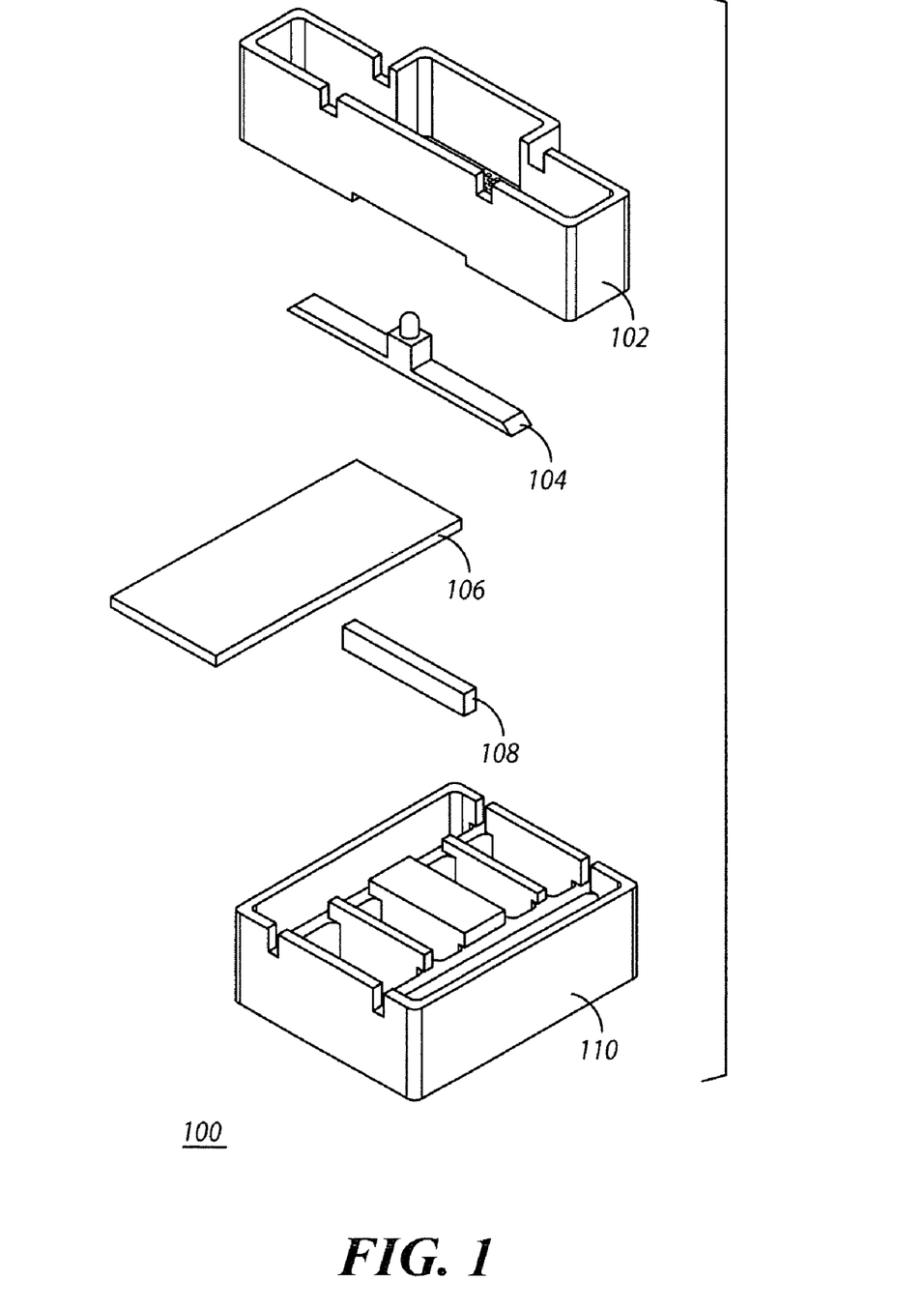
FIG. 1 is an exploded view of an ultrasonic test chamber in accordance with certain embodiments of the present invention.

An ultrasonic test chamber typically includes three functional sections: a de-bubbling station, a scanning station and a dryer. FIG. 1 shows an exploded view of an exemplary test chamber 100 in accordance with certain embodiments of the invention. The test chamber comprises a lower chamber 110 and an upper chamber 102. The chambers are held by a frame or housing (not shown) so that the gap between the two chambers may be adjusted to accommodate trays of varying thickness. In one embodiment, the lower chamber is fixed and the upper chamber may be raised or lowered. The upper chamber may house a moveable plate or scanning bar 104, the bottom of which is flush with the bottom of the upper chamber. An ultrasonic transducer is mounted in the scanning bar and can be independently moved up or down (relative to the lower chamber and relative to the scanning bar) to place the transducer at the proper distance from the parts. During operation, a parts tray 106 is passed beneath the transducer and plate. In a pulse echo ultrasonic scanner, the ultrasound from the transducer is pulsed and the echoes (reflections) from scanned parts is received by transducer. In a transmission system, a second ultrasonic transducer 108 may be mounted in the lower chamber 110 beneath the tray of parts 106, so that transmission of ultrasound through the parts may be measured. The ultrasonic transducers may, for example, comprise a single element transducer having a spot, line or flat focus (such as the Panametrics transducer part number A334S-SU), an array of transducers, one or more array transducers (such as the Imperium Inc., model DAV) or a combination thereof. The arrays may be line arrays, having a single dimension, area arrays having two dimensions or other arrangements of multiple transducers.

Figure 2:
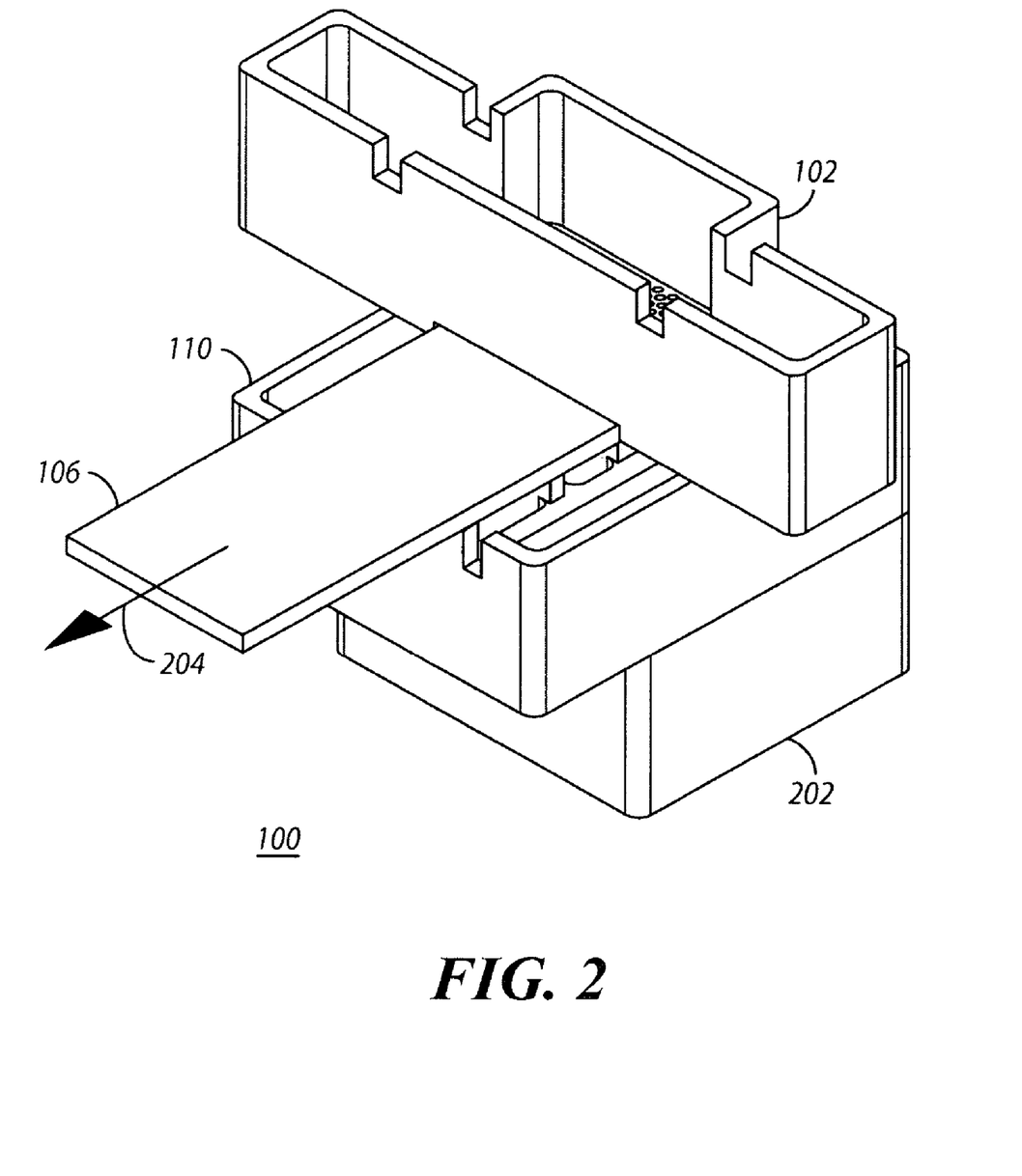
FIG. 2 is a further view of the ultrasonic test chamber shown in FIG. 1.

An assembled ultrasonic test chamber 100 is shown in FIG. 2. The upper chamber 102 is supported by a frame (not shown) so that the moveable plate or scan bar (104 in FIG. 1) is in close proximity to the upper surface of the parts in the tray of parts 106. The tray of parts 106 is moved in the direction of arrow 204 along a track, entering the right side of the chamber in the figure and exiting the left side. The tray may be propelled along the track by an arm connected to a screw drive, for example. The upper chamber is kept filled with a coupling fluid. Fluid is added at rate sufficient to compensate for the fluid lost through openings in the upper and lower chambers. Spilled fluid may be collected in a reservoir 202 and used to the refill the chambers. The re-filling can be performed by a pump, so that fluid is re-circulated from the reservoir to the upper and lower chambers. In this manner, the tray of parts may be maintained in a substantially horizontal position.

Figure 3:
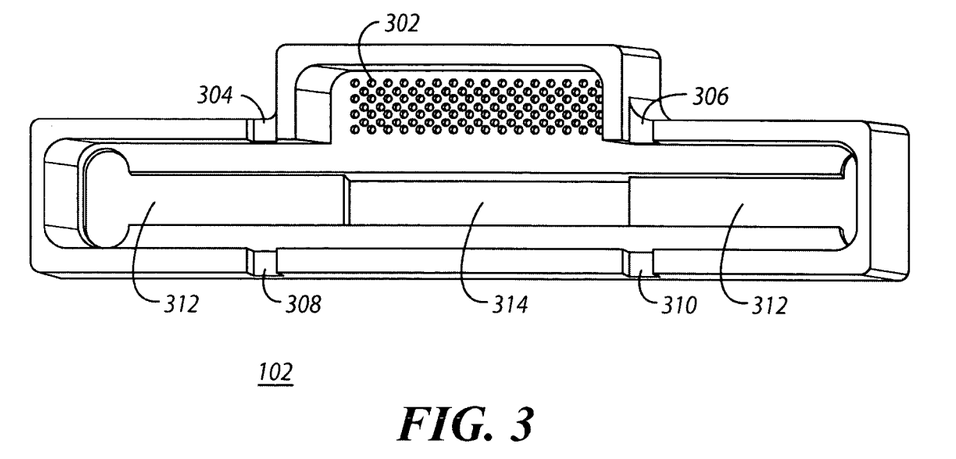
FIG. 3 is a diagrammatic representation of an exemplary upper chamber of an ultrasonic test chamber.

A more detailed view of the upper chamber 102 is shown in FIG. 3. The chamber is viewed from above. In use, the tray of parts first passes below a region of perforations or holes 302. In a further embodiment, the region 302 may contain a single slot. Region 302 is the de-bubbling region. Fluid is passed from below the parts and directed toward the underside of the parts so as to remove air bubbles. Excess fluid passes through the perforations or slot 302 and enters the upper chamber. Additional fluid may be added to the upper chamber as required. The perforations or slot are sized so as to prevent the parts from being dislodged by the fluid flow. Excess fluid may escape through one or more channels 304, 306, 308, 310, or through drain pipes (not shown). A track 312 is provided to guide the scanning bar 104. The scanning bar slides from left to right and right to left with the first transducer as it traverses the parts in the tray. The ultrasonic beam or transducer passes through opening 314. The parts in the tray are held in place by the scanning bar. In a further embodiment, the de-bubbling area and the scanning area may be separated.

Figure 4:
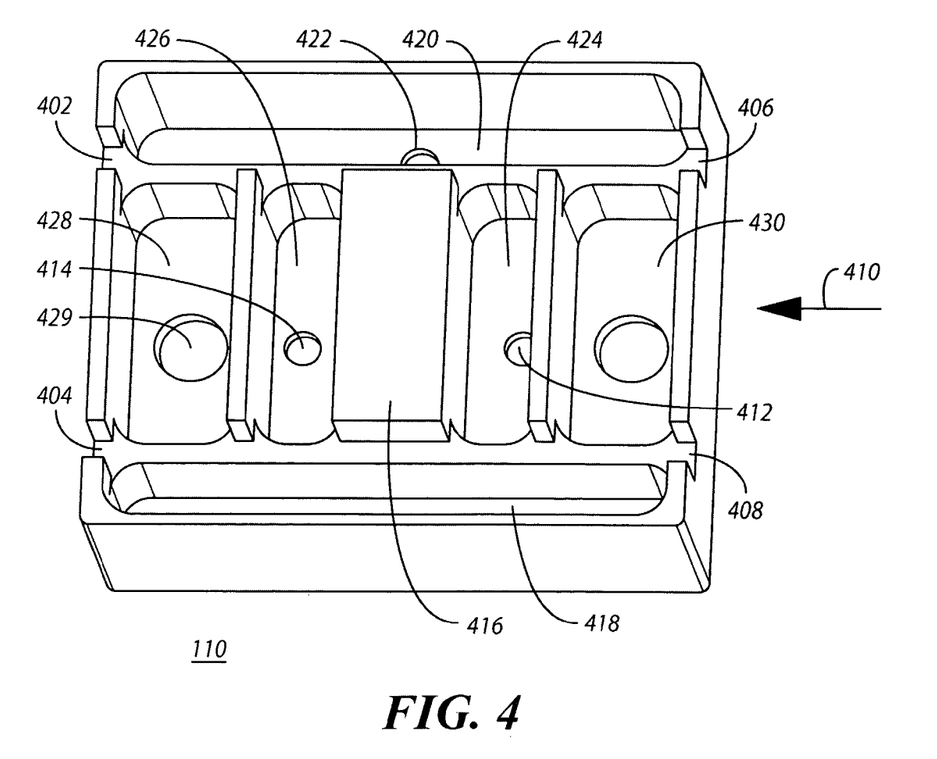
FIG. 4 is a diagrammatic representation of an exemplary lower chamber of an ultrasonic test chamber.

A more detailed view of an exemplary lower chamber 110 is shown in FIG. 4. The chamber is viewed from above. In use, the tray of parts enters on the right of the figure, moving in the direction of arrow 410. The lower chamber is positioned below the tray of parts 106 (not shown). The tray of parts moves along a track. One rail of the track lies in the slot between openings 402 and 406, the other lies in the slot between openings 404 and 408. In the embodiment shown in FIG. 4, the lower tray is symmetric so that parts may enter from the left or the right. If parts enter from the left, the upper chamber is rotated through 180°. The following description assumes that trays enter from the right in the figure. Chamber 430 is a copy of chamber 428 and is included to permit reversal of the tray movement. It is not necessary. De-bubbling chamber 424 is positioned below the de-bubbling region (302) of the upper chamber. Fluid is injected into the de-bubbling chamber 424 through the hole 412. The fluid may be injected at multiple locations. The injected fluid serves to dislodge air bubbles adhering to the underside of the parts in the tray. The tray then passes over the suction chamber 108. Drain chamber 426 is positioned after the scanning region. Fluid is drained from this region through opening 414. The region will typically contain both fluid and air, and will allow the underside of the parts to begin to dry. Finally the tray of parts enters the drying region above chamber 428. Air suction may be applied at opening 429 to help hold the parts in place. The parts are then dried by an air knife, hot air, a brush or by wicking materials (or a combination thereof). The brush or wicking materials are attached to the top side of the lower chamber or to the support frame. Side chambers 418 and 420 collect fluid spilled from the sides of the center chambers (424 and 426) and contain drain holes (422 for example) to allow the spilled fluid to be captured in the reservoir.

In a further embodiment, the upper and lower chambers are integrated, and height of the flat plate varied to accommodate trays of varying thickness.

The scanning station is where wetted and bubble-free parts are ultrasonically scanned. The ultrasonic transducer is moved across the parts at high speed in close proximity to the parts. The result is a motion in the fluid that tends to move the parts in the carriers or dislodge them from the carrier. Any motion in the fluid around the parts may tend to move the part in the carrier during the scan (which results in a blurred ultrasonic image) or dislodge the part entirely from the carrier. Hence, it is desirable to have some type of force holding the parts in to carrier. Since material other than the coupling fluid (typically de-ionized water) will have an acoustic impedance different to that of the coupling fluid, such material cannot be used between the part and the transducer, otherwise the ultrasonic image will be degraded. It is desirable for this force to be applied via the coupling fluid. In one embodiment of the invention, a fluid film is maintained above the parts in the carrier. This results in a net downward force on the parts that will tend to hold the parts in the carrier. In a further embodiment, suction may be applied beneath the tray of parts close to the scanning region. This further prevents the parts from being dislodged. These approaches may be used together to facilitate high speed scanning of the parts.

Figure 5:
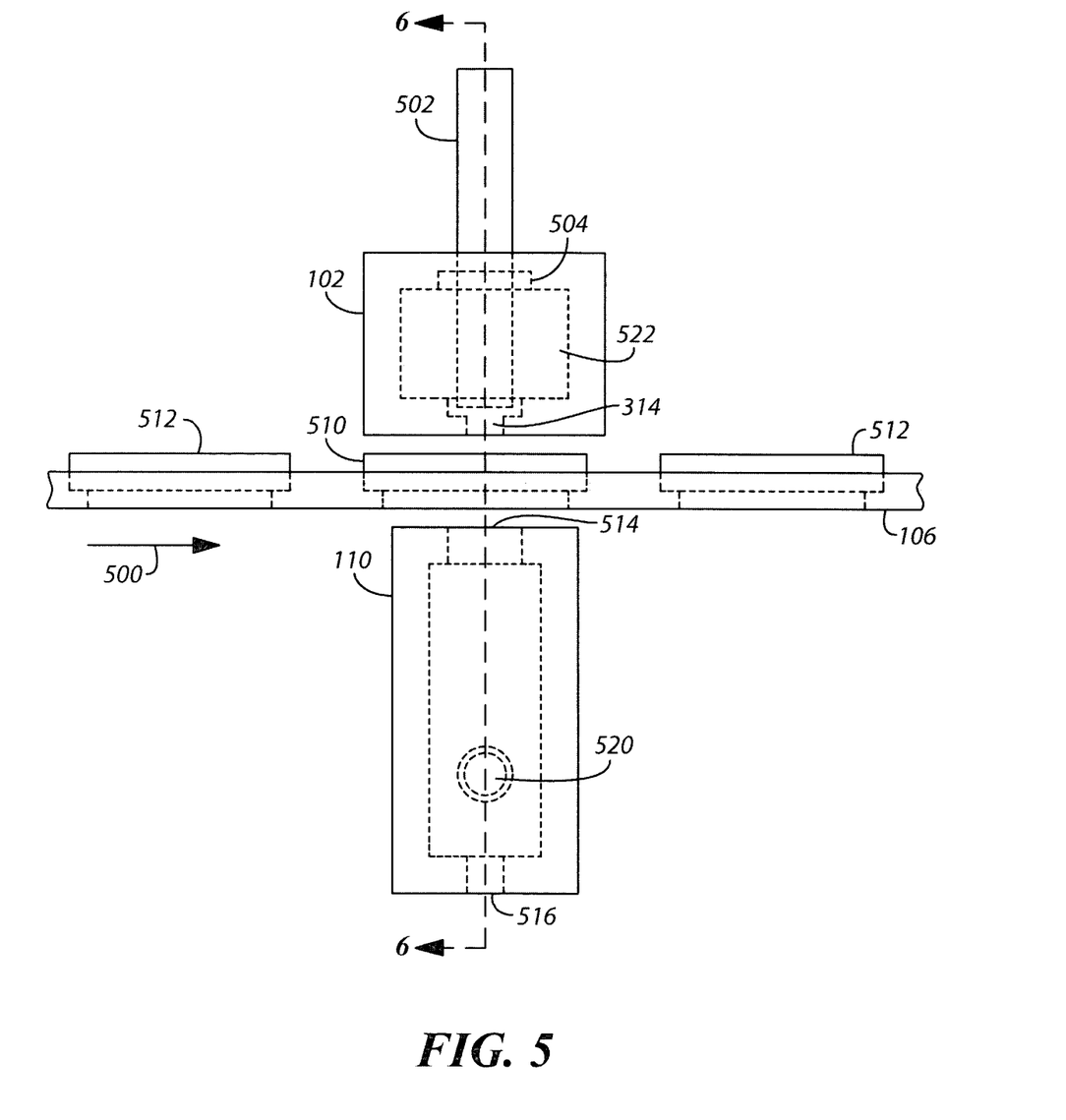
FIG. 5 is a diagram of an ultrasonic test chamber in accordance with certain embodiments of the invention.

FIG. 5 is a view of an embodiment of the present invention in which the upper chamber 102 moves with the transducer 502 during a scan. Referring to FIG. 5, the carrier 106 support parts 510, 512 and enters the scanning region in direction of arrow 500. An ultrasonic transducer 502 passes through an opening in the upper chamber 102. An optional seal 504 may be used to prevent significant leakage of coupling fluid from the hole around the transducer. The transducer may be moved up or down relative to the upper chamber to focus the ultrasonic beam. The upper chamber may be moved up or down to accommodate parts of various thicknesses. The cavity 522 the upper chamber is filled with coupling fluid. The ultrasonic beam passes through opening 314 in the upper chamber to insonify the object 510 being scanned. Ultrasound reflected from the object is sensed by the transducer 502 and used to identify the properties of the object 510. Coupling fluid is forced out of the upper chamber through one or more holes in its lower surface and flows across a part to be scanned 510. The coupling fluid forms a film of fluid between the top of the part 510 and the bottom surface of the upper chamber 102. This film provides acoustic coupling between the transducer and the part and also provides a downward force tending to hold the part 510 in place in the tray 106. The lower chamber 110 is placed such that an opening 514 in the top of the chamber is beneath the part 510 being scanned. Coupling fluid entering the lower chamber may drained through optional drain hole 516 and may be collected in a reservoir and re-circulated to the upper chamber. Air is drawn out of the lower chamber through hole 520, using a vacuum pump or a blower for example. This produces a suction force on the part 510 being scanned that tends to hold the part in the tray 106 and prevent it from being dislodged by motion of the upper chamber and transducer. When drain holes 516 is not present, the air and water mixture is drawn out through hole 520 and may be passed to an air/water separator so that the water can be collected and re-circulated.

Figure 6:
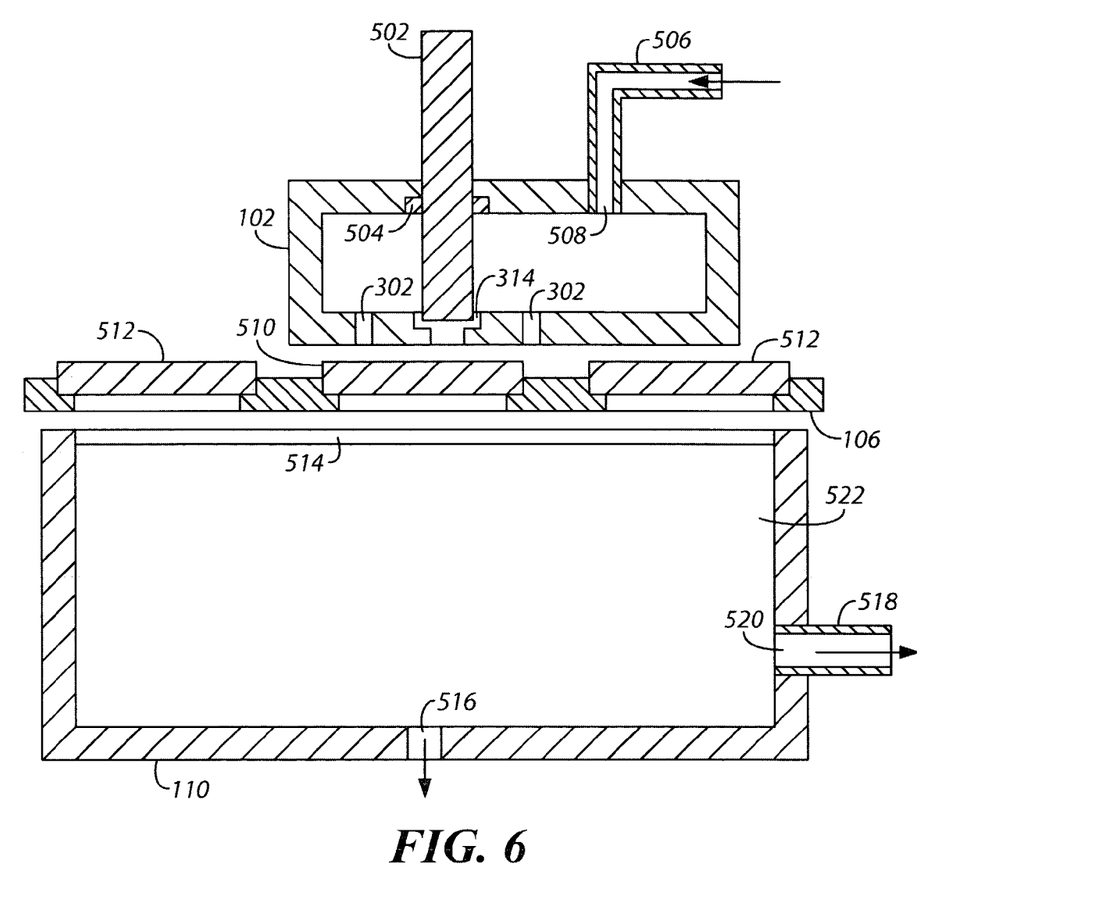
FIG. 6 is a cross sectional view of the ultrasonic test chamber in FIG. 5.

FIG. 6 shows a sectional view of the section 6—6 shown in FIG. 5. The parts tray 106 moves in a direction perpendicular to the plane of the figure. An ultrasonic transducer 502 passes through an opening in the upper chamber 102. A seal 504 may be used to prevent significant leakage of coupling fluid from the hole around the transducer. The seal 504 may be a rubber ring for example. The transducer may be moved up or down relative to the upper chamber to focus the ultrasonic beam. A coupling fluid supply pipe 506 supplies coupling fluid the upper chamber 102 through opening 508 at a rate sufficient to pressurize the fluid in the chamber and maintain an acoustic coupling between the lower (transmitting and receiving) end of the transducer 502 and the object to be scanned. The opening 314, through which the ultrasonic beam passes, may be recessed to allow the transducer to be moved close to the part 510 to be scanned. Coupling fluid is forced out of the upper chamber through holes 302 and flows across the upper surface of the part to be scanned 510. Coupling fluid may also flow from opening 314, depending upon the position of the transducer 502. The coupling fluid forms a film of fluid between the top of the part 510 and the bottom of surface of the upper chamber 102. This film provides acoustic coupling between the transducer and the part and also provides a downward force tending to hold the part 510 in place in the tray 106. The tray also holds additional parts 512. The upper chamber and transducer are moved in a scan path across the tray (left or right in the figure) perpendicular to the direction of motion of the tray to enable the other parts 512 to be scanned. The lower chamber 110 is placed such that an opening 514 in the top of the chamber is beneath the part 510 being scanned. The opening may extend across the width of the tray, as shown in the figure, so that the lower chamber may remain stationary during a scan. Alternatively, the lower chamber may be moved with the upper chamber during a scan. Coupling fluid entering the lower chamber is drained through drain hole 516 and may be collected in a reservoir and re-circulated to the upper chamber. Air is drawn out of the lower chamber via pipe 518 through hole 520. This produces a suction force on the part 512 being scanned that tends to hold the part in the tray 106 and prevent it from being dislodged by motion of the upper chamber and transducer.

The lower chamber may be used in conjunction with conventional transducer and coupling fluid arrangements. Also, the upper chamber may be used without suction being applied by the lower chamber. However, the retaining force on the part 510 will be greatest when the upper and lower chambers are used in conjunction.

Figure 7:
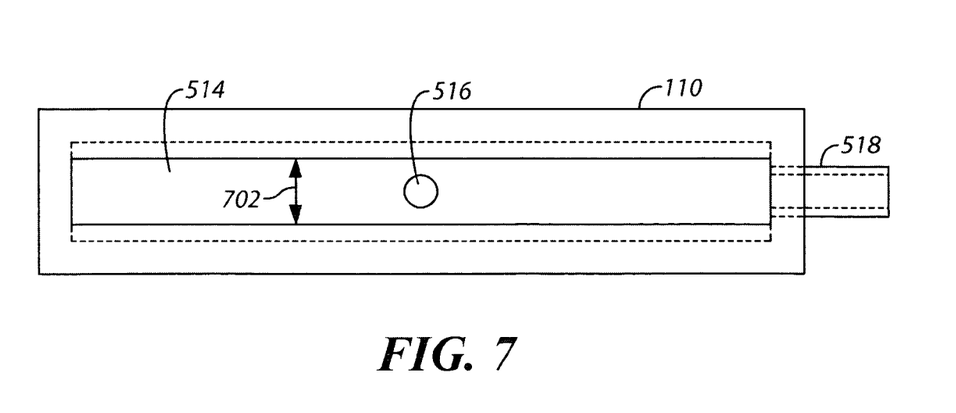
FIG. 7 is a top view of a lower chamber in accordance with certain embodiments of the invention.

FIG. 7 is a top view of a lower chamber 110. An opening 514 in the top of the chamber allows air to be drawn into the chamber past the parts being scanned. The hole 516 allows coupling fluid entering the chamber to be drained. Air is sucked out of the chamber through pipe 518 by a vacuum pump (not shown). The dimension of the opening 702 and the rating of the vacuum pump are selected to maintain sufficient suction on the part being scanned.

While the invention has been particularly shown and described with reference to exemplary embodiments, it will be understood by those skilled in the art that various changes in form and detail may be made therein without departing from the spirit and scope of the invention. In addition, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

Figure 8:
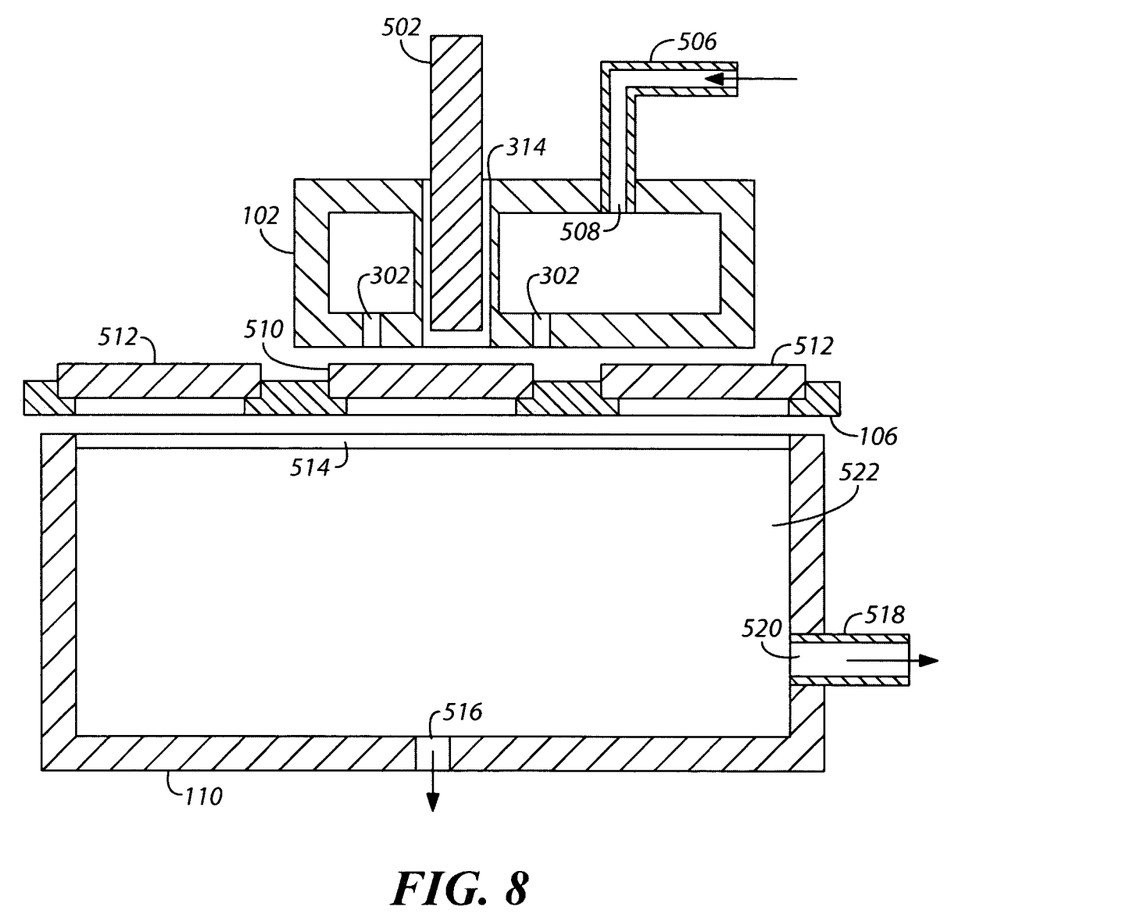
FIG. 8 is a cross sectional view of a further embodiment of an ultrasonic test chamber.

FIG. 8 shows a sectional view of an alternative embodiment of the upper chamber. In this embodiment the ultrasonic transducer 502 passes through a passage 314 in the upper chamber 102. Coupling fluid flows from the interior of the upper chamber 102 to the surface of the part 510 through holes 302. The coupling fluid also tends to flow up the passage 314 around the transducer 502, aided by capillary action. In this manner, a fluid coupling is maintained between the end of the transducer 512 and the part 512 being scanned.

What is claimed is:

1. A method for ultrasonic scanning of an object in a scanning station, the scanning station having upper and lower chambers, the upper chamber being positioned above the lower chamber and vertically spaced therefrom, the method comprising:
   moving the object between the upper and lower chambers;
   insonifying the object with ultrasound from an ultrasonic transducer having an ultrasound emitting surface;
   supplying a coupling fluid to the upper chamber so that coupling fluid flows through one or more holes in the bottom of the upper chamber to the upper surface of the object, thereby filling the space between the ultrasound emitting surface of the ultrasonic transducer and the object;
   applying suction from the lower chamber to hold the object in place while it is insonified; and
   sensing ultrasound reflected from the object,
   wherein applying suction from the lower chamber comprises
   positioning the part above a first opening in a lower chamber; and
   operating a blower coupled to a second opening in the lower chamber to remove fluid from the lower chamber.

2. A method in accordance with claim 1, wherein moving the object comprises moving the object along a substantially horizontal track attached to the lower chamber.

3. A method in accordance with claim 1, further comprising adjusting the distance between the upper and lower chambers in accordance with the thickness of the object.

4. A method in accordance with claim 1, further comprising moving the ultrasound emitting surface of the ultrasonic transducer in a vertical direction within the upper chamber to focus the ultrasound.

5. A method in accordance with claim 1, further comprising collecting coupling fluid in the lower chamber and re-circulating the coupling fluid to the upper chamber.

6. A method in accordance with claim 1, wherein applying suction in the lower chamber beneath the object comprises drawing air out of the lower chamber.

7. A method in accordance with claim 1, wherein the object is a part in a carrier supporting one or more parts.

8. A method in accordance with claim 7, wherein moving the object comprises moving the carrier in a first horizontal direction along a substantially horizontal track attached to the lower chamber.

9. A method in accordance with claim 7, further comprising moving the upper chamber and ultrasonic transducer in a horizontal scan path across the carrier.

10. A method in accordance with claim 8, further comprising moving the lower chamber with the upper chamber in a horizontal scan path.

11. A method for retaining a part in a carrier during ultrasonic scanning, the method comprising:
    positioning the part in the carrier above a first opening in a lower chamber; and
    drawing air through a gap between the carrier and the lower chamber and out of a second opening in the lower chamber using a blower coupled the lower chamber via a tube,
    whereby suction is applied to retain the part in the carrier.

12. A method in accordance with claim 11, wherein positioning the part comprises moving the carrier along a track.

13. An ultrasonic scanner for use in inspecting an object, comprising:
    an upper chamber operable to dispense coupling fluid to the upper surface of the object;
    a lower chamber being located below the upper chamber and spaced from it to allow the object to pass between the upper chamber and the lower chamber, the lower chamber have a first opening located below the upper chamber;

a blower coupled to a second opening in the lower chamber and operable to draw fluid into the lower chamber through the first opening in the lower chamber and thereby provide suction below the object when the object is placed between the upper and lower chamber in proximity to the second opening of the lower chamber; and an ultrasonic transducer located within the upper chamber, wherein coupling fluid is supplied to the upper chamber at a sufficient rate to provide fluid coupling between the ultrasonic transducer and the object.

14. An ultrasonic scanner in accordance with claim 13, wherein the upper chamber and ultrasonic transducer are moveable in a horizontal scan path.

15. An ultrasonic scanner in accordance with claim 13, wherein the ultrasonic transducer is moveable in a vertical direction within in the upper chamber.

16. An ultrasonic scanner in accordance with claim 13, wherein the object is a part in a tray of parts.

17. An apparatus for retaining a part in a carrier during an ultrasonic scan, comprising:

a lower chamber having a first opening at the top of the chamber and a second opening;

a suction means for drawing air out of the second opening of the lower chamber, and a positioning means for positioning the carrier such that the part is above the first opening of the lower chamber and sufficiently close thereto that suction is applied below the part, wherein the suction means comprises a blower coupled to the second opening in the lower chamber and operable to draw fluid through lower chamber, the fluid entering the lower chamber through the first opening in the lower chamber and exiting the lower chamber through the second opening in the lower chamber.

18. An apparatus in accordance with claim 17, wherein the positioning means moves the carrier in a first horizontal direction along a track.

19. An apparatus in accordance with claim 18, wherein the lower chamber extends the width of the carrier, perpendicular to the first horizontal direction.

20. An apparatus in accordance with claim 17, further comprising an ultrasonic transducer having an ultrasound emitting surface and being moveable in a horizontal scan direction and in a vertical direction.

21. An apparatus in accordance with claim 20, further comprising an upper chamber positioned above the carrier and surrounding the ultrasound emitting surface of the ultrasonic transducer, wherein the upper chamber contains coupling fluid that is discharged onto the part in the carrier.

* * * * *